United States Patent [19]

Mertzweiller et al.

[11] 3,932,547

[45] Jan. 13, 1976

[54] HYDROGENATION OF ORGANIC COMPOUNDS

[75] Inventors: Joseph K. Mertzweiller; Horace M. Tenney, both of Baton Rouge, La.

[73] Assignee: Exxon Research and Engineering Company, Linden, N.J.

[22] Filed: Aug. 22, 1974

[21] Appl. No.: 499,793

Related U.S. Application Data

[60] Division of Ser. No. 253,765, May 16, 1972, Pat. No. 3,855,324, which is a continuation-in-part of Ser. No. 880,993, Nov. 28, 1969, Pat. No. 3,711,423, which is a continuation-in-part of Ser. No. 674,098, Oct. 10, 1967, abandoned.

[52] U.S. Cl. ............... 260/667; 260/638; 260/683.9
[51] Int. Cl.² ......................................... C07C 5/10
[58] Field of Search ...................... 260/683.9, 667

[56] References Cited
UNITED STATES PATENTS

| | | | |
|---|---|---|---|
| 3,677,969 | 7/1972 | Mertzweiller et al. | 252/430 |
| 3,677,970 | 7/1972 | Mertzweiller et al. | 252/430 |
| 3,758,614 | 9/1973 | Mertzweiller et al. | 260/667 |
| 3,770,844 | 11/1973 | Mertzweiller et al. | 260/667 |

*Primary Examiner*—Herbert Levine
*Attorney, Agent, or Firm*—J. Simon; John W. Ditsler

[57] ABSTRACT

Novel hydrogenation catalysts are formed by impregnating a suitable support material with an aqueous solution of a salt of a transition metal; heat-treating the impregnated support at a temperature above 500°F. to form chemical complexes on the surface of the support and to drive off moisture and absorbed oxygen; activating the surface complex by contacting the impregnated support with a soluble organometallic compound wherein the metal constituent is selected from Groups I, II and III of the Periodic Chart of the Elements, and thereafter treating the activated support material in the presence of a gaseous stream containing hydrogen at a temperature of at least 300°F. to form a highly stable heterogeneous catalyst. The novel supported catalysts of the instant invention have been found to be highly active for the hydrogenation of organic compounds under extremely mild conditions.

16 Claims, No Drawings

3,932,547

HYDROGENATION OF ORGANIC COMPOUNDS

CROSS-REFERENCE TO RELATED APPLICATION

This application is a division of U.S. Pat. Ser. No. 253,765, filed May 16, 1972 now U.S. Pat. No. 3,855,324 which in turn is a continuation-in-part of U.S. Ser. No. 880,993, filed Nov. 28, 1969 now U.S. Pat. No. 3,711,423 which in turn is a continuation-in-part of U.S. Ser. No. 674,098, filed Oct. 10, 1967, now abandoned.

BACKGROUND OF THE INVENTION

This invention relates to a new and useful process for the preparation of high activity catalysts suitable for reactions between hydrogen and hydrocarbons and particularly for the hydrogenation, or hydrogen addition, to organic compounds containing nitrile groups, carbonyl groups, aromatic, acetylenic or olefinic linkages. It is also concerned with the novel catalysts so produced, as well as the processes for using these catalysts.

DESCRIPTION OF THE PRIOR ART

Various heavy metals, especially transition metals, have been previously described as useful for conducting catalytic reactions. Hydrogenation catalysts have included solid metals, slurries of metals, and metals dispersed on supports. Solid metal catalyst had been prepared by contacting oxides of the desired metal with reducing gases, e.g., carbon monoxide, or hydrogen, or both. Slurries suitable as catalyst have been prepared by contacting anhydrous solutions of organometallic compounds of the desired metal with organoaluminum compounds, these being brought together to form slurried catalysts. Metals have been provided on supports by impregnation of support with anhydrous solutions of the salts of the desired metal, this being found by reduction of the salts to produce deposition of metallic metal.

In Canadian Pat. No. 697,780, which issued Nov. 10, 1964, methods are described for improving the activity of cobalt and for converting certain inactive metals, i.e., manganese and molybdenum, into hydrogenation catalysts. In typical reactions, slurried catalytic mixtures are produced by forming anhydrous solutions of soaps of the desired metal, and the desired organometallic reducing agent, and then contacting the two solutions together to form catalytic reaction mixtures. In accordance with one of the methods, a support is impregnated by contact with anhydrous or nonaqueous solution of a soap of the desired metal, and with an organometallic reducing agent, such as organoaluminum compound, to produce a loosely supported reaction product mixture of dispersed metals. In other techniques, supports are impregnated with soaps of the desired metal, and the support then contacted with a solution of the organometallic reducing agent to produce supported catalytic mixtures.

While these catalysts are moderately active hydrogenation catalysts, there are nonetheless a number of diasvantages associated with their use. For one thing, the materials, in all the phases of their use are highly pyrophoric and the slurries must be formed in an oxygen-free atmosphere. Also, the catalytic materials formed are highly pyrophoric. Thus, the catalytic product of the reaction is an insoluble pyrophoric solid which is highly reactive whether in slurry or supported form. Moreover, the material used in forming the catalysts are quite expensive, to say nothing of the cost involved, due to the extra precautions which must be taken in handling the materials. Furthermore, the organic solvents which are used are highly flammable.

In U.S. Pat. No. 3,415,759 there is dsclosed a method for preparing a hydrogenation catalyst by depositing cobalt carboxylate on a diatomaceous earth support and heating the supported cobalt carboxylate at a temperture between about 135° and 160°C. and thereafter reacting the thus heat-treated product with an aluminum alkyl. However, when temperatures materially above about 160°C. are employed to dry the catalysts, the catalyst becomes progressively deactivated, particularly insofar as the hydrogenation of high molecular weight compounds are concerned.

SUMMARY OF THE INVENTION

It has now been discovered that novel hydrogenation catalysts exhibiting unusually high activity and stability may be prepared by impregnating a suitable support material, as hereinafter defined, with an aqueous solution of a salt of a transition metal; heat-treating the impregnated support at a temperature of at least about 500°F. to form chemical conplexes on the surface of the support and to drive off moisture and absorbed oxygen; activating the surface complex by contacting the impregnated supports with a soluble organometallic compound wherein the metal constituent is selected from Groups I, II and III of the Periodic Chart of the Elements, and thereafter treating the activated support material in the presence of a gaseous stream containing hydrogen at a temperature of at least 300°F. The present invention is based on the discovery that a highly tenaceous chemical bonding can be formed between the surface of certain types of supports and the transition metals and the metallic constituent of the soluble organometallic compound when the metals are applied to the supports under the sequence and critically defined conditions of the instant invention. In the sequence of process steps, a supporting material having a surface area of at least 5 square meters per gram and containing at least 0.1 millimoles of hydroxyl groups per gram of support is first impregnated with a water-soluble species of a transition metal, preferably a Group IB, IVB, VB, VIB, VIIB or Group VIII metal. Water has been found particularly suitable for the application of the Group IB, IVB, VB, VIB, VIIB or Group VIII metals to the support by contacting or immersing the support in an aqueous solution of a salt of the desired metal. Suitably, the support is impregnated with from about 0.1 to about 20% metal, and preferably from about 2 to about 10% metal, based on the total weight of the deposited metal and support.

The impregnated support is then preconditioned by heating the impregnated support at a temperature of at least about 500°F. in order to drive off moisture and absorbed oxygen from the catalyst surface. The preconditioned catalyst is then activated by contacting the impregnated supports with a soluble organometallic compound wherein the metallic constituent is selected from Groups I, II and III of the Periodic Chart of the Elements and wherein the metallic constituent has an atomic number of from 3 to 50. Preferably, the organic constituents of the organometallic compound are alkyl groups, particularly linear alkyl groups having from 1 to 12 carbon atoms. Only the organometallic compounds of Groups I, II and III which are soluble in hydrocarbons or soluble in, or complex with ethers are suitable for the method of this invention. These are the organometallic species which are characterized by predominantly covalent bonding between the metal and the alkyl and/or hydride groups. The preferred metallic constituent of the organometallic compound is aluminum.

Thereafter, the activated support material is treated by heating the activated supported material at a temperature of at least 300°F in the presence of a gaseous stream containing hydrogen. Preferably, the activated supported material is treated in the presence of hydrogen at a temperature above 800°F. and more preferably at a temperature in the range of from about 800° to about 1200°F. for a period of time in the range from about 1 to about 100 hours. Surprisingly, it has been found that under these high severity conditions, i.e., treating the activated supported catalyst at a temperature above 800° and up to about 1200°F. in the presence of hydrogen, the activity of these catalysts is not significantly decreased and, in fact, generally increases as the treating severity is increased.

While the exact nature of the mechanism is not known and, though the applicants do not wish to be bound by a specific theory on mechanism, there are certain things which are known to occur in the formation of these catalysts. When a suitable support has been impregnated with a transition metal and heat-treated at a temperature of at least 500°F., there is believed to exist a chemical bonding between the surface of the support and the species of the transition metal. This interaction is believed to occur between the acid sites on the support surface and the transition metal salt. Evidence of such interaction is obtained when, for example, iron is employed as the transition metal and is impregnated on a suitable support and heat-treated at a temperature of 500°F. in accordance with the practice of the instant invention, and examined by Mossbauer spectroscopy. Such an examination reveals that essentially all i.e., 99+%, of the iron is in the +3 valence state and the Mossbauer pattern corresponds to no known oxide of iron nor to the iron salt employed in impregnating the suitable supporting material. Consequently, this interaction or chemical bonding between the support and the transition metal is believed to be responsible for the difficulty in reducing such a supported catalyst to metallic iron by treatment with hydrogen. For example, under conditions of 1 atmosphere hydrogen pressure at a temperature of about 1000°F., virtually all the iron is reduced to the +2 valence state, i.e., an inactive catalyst while little or no metallic iron is formed.

However, when the heat-treated impregnated support is treated with an excess organometallic compound, for example, triethylaluminum, it is believed that the bond between the iron and the support is reduced by the organometallic compound with the organometallic, i.e., metal alkyl fragment being bonded to the support and replacing the reduced iron. Consequently, when the activated supported catalyst is then treated in the presence of hydrogen under increasingly sever conditions, two reactions are believed to occur: (1) further reduction of the transition metal species to a lower valence species or to the "nascent metal" state, and (2) simultaneous removal of the functional groups, i.e., alkyl and hydride groups, from the metal alkyl fragments resulting in bonding between the alkyl metal and the transition metal. The abovedescribed reactions can be visualized as follows:

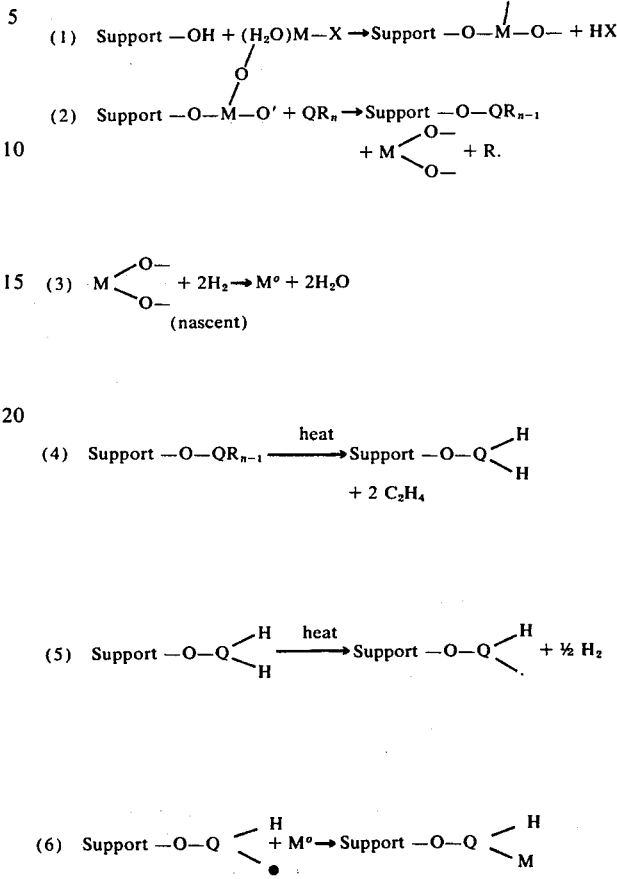

wherein M–X represents the transition metal salt impregnated upon a suitable support, as hereinafter defined, by aqueous solution; M thus representing the transition metal; where Q represents a Group I, II or III metal and R represents hydride or the organic constituent of the organometallic compound and wherein n is equal to the valence state of Q.

The free radical Ro resulting from equation (2) must stabilize itself by combination or disproportionation. When R is an ethyl radical, the combination product is n-butane and the disproportionation products are ethylene plus ethane. The gas liberated when these catalysts are treated with an organometallic compound, i.e. triethyl aluminum is predominantly ethane but containing appreciable amounts of ethylene and n-butane. Evidence for reactions (4) and (5) has been obtained by treating typical gamma alumina supports with triethyl aluminum (no transition metal present) and analyzing the gases liberated when the treated alumina is heated at temperatures of 400°–1200°F. Reaction (6) represents bonding between a radical resulting from thermal decomposition of the Q metal hydride and an electron (probably a d-electron) supplied by the transition metal in a reduced valence state.

While the exact nature of this bonding is unknown, it is believed that the product of reaction (6) which is believed to be a close approximation to the active sites of these catalysts, is a stable bond which accounts for the increased activity and inhibition of crystallite growth on the surface of the catalyst when the catalysts are subjected to high temperatures in the presence of hydrogen. Closely related configurations such as:

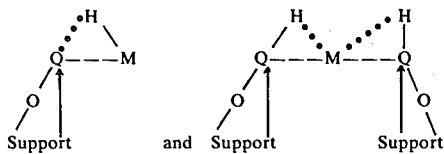

can easily be formed from the product of reaction (5) to give the iron a +2 valence state which has been observed in several cases for these catalyst systems by Mossbauer and magnetic susceptibility. As disclosed above, a critical feature of the instant invention is the conditions under which the activated supported catalyst is treated with a gaseous stream containing hydrogen. In terms of the mechanism disclosed above, this "fixation" treatment is believed to favor the completion of reactions (3), (4), (5) and (6). In this manner catalysts several orders of magnitude more active and more stable than those described in prior art processes are obtained.

Thus, it is believed that the applicants have discovered a new route to a valuable and novel heterogenous catalyst which is believed to involve chemical bonding between the support, transition metal and metallic constituent of the organometallic reducing agent which allows for a highly active catalyst which is stable under high severity conditions.

The selection of a suitable support material upon which the transition metal is impregnated as an essential feature of the instant invention. Suitable supports are those having a reasonable surface area and a sufficient concentration of hydroxyl groups on the surface, which hydroxyl groups are capable of reacting with an organometallic compound, i.e., $QR_n$ or $QR_nX_n$, where Q represents a Group I, II or III metal, R represents hydride or an organic constituent, e.g., an alkyl group of the organometallic compound, and wherein X equals a halogen, in order to eliminate the RH species and attach the $QR_{n-1}$ species to support surface through the oxygen atom of the original hydroxyl group. Properties and suitability of supports can be characterized in terms of surface area and their hydroxyl content measured by reaction with an organometallic i.e., $QR_n$ compound in the absence of a transition metal.

Those supports most suited to the instant invention include the oxides of Groups II, III and IV of the Periodic Chart of the Elements which can be prepared with surface areas in excess of 5 square meters per gram and wherein the hydroxyl content of the support is at least 0.1 millimoles of hydroxyl groups per gram of support. The oxides of Groups, II, III and IV having a surface area in excess of 50 square meters per gram and containing a hydroxyl group content of at least 0.2 millimoles of hydroxyl groups per gram of support, determined by reaction of the support with the organometallic compound in the absence of the transition metal are preferred. Aluminum oxide having a surface area of above about 100 square meters per gram and a hydroxyl content of at least 1 millimole per gram is the most preferred supporting material of the instant invention. Additional, nonlimiting examples of suitable supporting materials include magnesium oxide, zinc oxide, titanium oxide, provided they have the necessary surface areas and reactive hydroxyl group content as described above. Any types of supports, while possessing the desired surface area, may or may not have the desired reactive hydroxyl group content. Nevertheless, some such supports, for example, activated carbon, can be enhanced in hydroxyl group content by treatment with air or an air-stream mixture at moderate temperatures, i.e. below about 1000°F. in order to form a suitable support for the catalyst of the instant invention. Other well-known supports, such as silica, have a sufficient surface area but may lack the necessary concentration of reactive hydroxyl groups and are not suitable. Silica-alumina supports, having the necessary hydroxyl group concentrations are effective supports and may also be employed in the practice of the invention.

The supported catalyst of the instant invention may be prepared by any means conventionally used for the preparation of a supported catalyst, e.g., by impregnating the support or by precipitation in the presence of the support or by coprecipitation with the supporting material. Water has been found to be particularly suitable for the application of the transition metal salt to the supporting materials. Preferably, the support is first impregnated with a water-soluble species of the transition metal salt by contacting or immersing the support in an aqueous solution of the salt of the desired metal. Preferably, the support is impregnated with from about 0.1 to about 30% equivalent transition metals; and preferably from about 1 to about 10% equivalent transition metal, based on the total weight of the deposited equivalent metal and support. The optimum concentration of transition metal on the support will depend on the nature of the transition metal and on the surface area and hydroxyl content of the support. For example, when a pure activated alumina having a surface area of about 200 square meters per gram and a hydroxyl content of about 1.2 millimoles per gram is employed as the supporting material, and when iron is employed as the transition metal, the optimum concentration of iron is about 0.6 millimoles of iron per gram support. With noble metals, for example much lower concentration in the range of 0.1 to 1% are employed. The optimum concentration for other transition metals which results in the highly active, stable catalysts of the instant invention are not shown with exactitude because of the many and varied supports which can be employed herein. Nevertheless, it is believed that one skilled in the art can readily determine these concentrations in view of the fact that they are within the preferred concentration ranges as described above.

The use of water to effect the chemical bonding is particularly important in the impregnation of the supports with salts of the desired transition metal. Even iron has produced an exceptionally active catalyst when applied to the support in the form of salts dissolved in aqueous solution. In fact, catalysts derived from aqueous solutions of iron salts have ever proved highly effective for the hydrogenation of aromatic nucleus and carbonyl groups of organic compound, i.e. aldehydes and ketones.

The transition metals which can be employed in the practice of the instant invention include the Groups IB, IVB, VB, VIB, VIIB and Group VIII metals. Preferably, the transition metals which can be employed in the practice of the instant invention include iron, cobalt, nickel, platinum, tungsten, chromiun, vanadium, molybdenum, rhenium, manganese, titanium, zirconium, palladium, rhodium, copper, silver and gold. The most preferred transition metals include iron, cobalt and nickel, platinum, tungsten, chromium, molybdenum, vanadium, rhenium and copper. Nonlimiting examples of salts which can be employed for the application of these metals to these supports include the halides, sulfates, nitrates, formates, acetates, propionates, molybdate, vanadates, chromates, dichromates, tungstates, manganates, titanates, zirconates, rhenates, perhenates and the like. Water soluble acids such as perrhenic acid may also be employed. These various transition metals described above may be used alone or in combination.

The impregnated support in powder or granular form, is then treated by establishing time-temperature relationships suitable to produce a chemical change on the surface of the support and remove water and absorbed oxygen. Suitably, the impregnated support can be heated in air, in an inert atmosphere or in vacuum, e.g. 20 to 29 inches of vacuum at a temperature of at least about 500°F. preferably 600° to 1500°F. and more preferably from about 600° to about 1000°F. It is a critical feature, in order to form the more highly active and stable catalyst of the instant invention, to heat the impregnated support at a temperature above 500°F. for a period of time in the range of about 0.5 to about 4 hours and preferably from about 1 to 2 hours. While the heat-treatment may be performed in air or an oxygen atmosphere, it must then be followed by a period in an inert atmosphere in order to remove the adsorbed oxygen. In addition to the removal of oxygen and moisture, other important reactions occur during this heat-treatment, as described above, in order to render the transition metal in a form more amenable to the subsequent reaction with the organometallic compounds.

In an alternative embodiment, the impregnation and heat-treating steps can be conducted in multiple stages. For example, the support can be impregnated and then dried or partially dried, at low temperature. The support can then be reimpregnated and again dried or partially dried. The heat treatment per se may be conducted in multiple stages, if desired. The impregnated support, to facilitate handling, can thus be subjected to a first rather mild heat treatment to dry the support and then, in a second step, to a more severe treatment to produce the desired chemical change at the surface of this support. Supported catalysts, such as are supplied by the commercial catalyst manufacturers, e.g., iron, cobalt and/or nickel, alone or in combination with other metals such as molybdenum, tungsten, or the like are also amenable to such tretments to transform them to highly active catalysts.

The then impregnated, heat-treated support is activated by treatment with an organometallic compound, suitably a hydrocarbon solution of an organometallic compound, or a hydrocarbon soluble organometallic compound, a metallic constituent of which is selected from Groups I, II and III of the Periodic Chart of the Elements as in Fisher Scientific Company Copyright 1952. Preferably, the oroganometallic compounds include those having the formula: $QR_n$ wherein Q is equal to the metallic constituent and is selected from Groups IA, II and IIIA having an atomic number of from 3 to 50, n is the valence state of Q and wherein R is hydride or an organic constituent selected from the group consisting of same or different, substituted or unsubstituted, saturated or unsaturated alkyl, aryl, alkylaryl, arylalkyl or cycloalkyl groups containing up to about 20 carbon atoms. Representative, nonlimiting examples of the organic constituents, i.e. R include, but are not limited to methyl, ethyl, n-propyl, isopropyl, isobutyl, secondary butyl, tertiary butyl, n-amyl, isoamyl, heptyl, n-octyl, n-dodecyl and the like; 2-butyl, 2-methyl-2-butyl, and the like; cyclopentylmethyl, cyclohexyl-2-butyl, cyclohexyl-propyl and the like: 2-phenylethyl, 2-phenylpropyl, 2-naphthylethyl, methylnaphthylethyl and the like; cyclopentyl, cyclohexyl, 2,2,1-bicycloheptyl and the like; methylcyclopentyl, dimethylcyclopentyl, ethylcyclopentyl, methylcyclohexyl, dimethylcyclohexyl, 5-cyclopentadienyl and the like; phenylcyclopentyl, and the like, phenyl, tolyl, ethylphenyl, xylenyl, naphthyl, cyclohexylphenyl and the like. The more preferred metallic constituent of the organic metallic compound, i.e., Q is selected from the group consisting of lithium, magnesium, beryllium, zinc, cadmium, mercury, boron aluminum, gallium and indium. In addition, organometallic compounds having the formula $QR_nX_m$ may be employed as the organometallic compound of the instant invention where Q and R are identical to the Q and R having been previously described, X is a halogen, and $n$ and $m$ are integers ranging from 1 to 3, the summation equal to the valence of Q.

The most preferred organometallic activating agents are the tri-alkyl substituted products of aluminum and the dialkyl halides of aluminum, particularly those containing alkyl groups having from one to about 6 carbon atoms, especially the linear alkyl groups. Exemplary of such compounds, which contain up to about 18 carbon atoms in the molecule, are trimethyl aluminum, triethyl aluminum, tri-n-butyl aluminum, triisobutyl aluminum, diethyl aluminum hydride, diethyl aluminum chloride, diethyl aluminum fluoride and the like. Certain volatile or hydrocarbon-soluble hydrides, for example, the various known hydrides of boron, are also suitable activating agents as well as are the Grignard reagents.

The treatment of the supported, heat-treated catalyst with the organometallic compound can be carried out with pure or diluted metal alkyl compounds in the liquid or vapor phase. Hydrocarbon diluents of the paraffinic, cyclo-parafinic or aromatic types are entirely suitable. The metal alkyl compound may be present in concentrations of 5 to 50% in the diluent. A solution of about 20% aluminum triethyl in a paraffinic diluent is a preferred activation system. The activation reaction is quite exothermic and it may be desirable to remove the heat of activation. The temperature during the activation step, which is maintained in the range of from about 0°F. to about 500°F., preferably from about 100°F. to about 200°F. Considerable gas liberation occurs during activation and these gases are normally vented from the system. The activation is allowed to proceed until reaction is no longer observed, generally 0.5 hrs. to 2 hrs. in contact with at least some excess of metal alkyl compound.

The treatment of the activated support material in order to obtain the most active and stable catalysts referred to above as the "fixation" step in a critical feature of the instant invention. After the supported catalyst has been activated with the organometallic reducing agent, it is essential that the supported catalyst be treated in the presence of a gaseous stream containing hydrogen at a temperature of at least 300°F. in order to form the highly active, stable, novel heterogeneous catalyst of the instant invention. Preferably, the supported activated catalyst is treated in the presence of hydrogen at a temperature in the range of from about 300°F. to about 1200°F., more preferably from about 400°F. to about 1200°F. and still more preferably between about 800°F. and 1200°F. It is essential that this fixation treatment be conducted in the presence of a gaseous stream containing hydrogen. This fixation treatment can be carried out in the presence of inert gases such as nitrogen, helium, argon, and the like in view of the fact that hydrogen is formed " in situ" when these inert gases are employed. Necessarily, however, the fixation in the presence of such inert gases as nitrogen, helium, and argon will result in catalysts of lower activity than when the fixation step of the activated supported catalyst is conducted totally in the presence of a hydrogen gas.

Although nitrogen is normally considered an inert gas, there is evidence that it may not be truly inert when present in the fixation of these catalyst systems. There is some evidence that gaseous nitrogen may react with the transition metal species at elevated temperatures. Such reaction which may form nitrides of the metals are obviously undesirable. Therefore, it is preferred that the fixation step be conducted at the above critical temperatures in the presence of a gaseous stream containing or resulting in the formation in the reaction zone of from about 5 to 100% hydrogen and more preferably from about 75 to about 100% hydrogen. Most preferably, the fixation under the above-described critical temperature conditions is conducted totally in the presence of a hydrogen atmosphere. As described above, it is believed that the function of hydrogen during the "fixation step" when the supported activated catalyst is treated under the critical temperature limitation described above, is to fix the catalyst in a stable heterogeneous form and to further reduce the transition metal compound to a valence state to which it can more readily and completely react the metallic portion of the organometallic compound.

The fixation of the supported activated catalyst in the presence of a hydrogen gas under the above-described critical conditions is usually conducted over a period of time varying between about 1 to about 100 hours, generally less time being required at higher temperatures. As described above, it is quite surprising that under optimum conditions as described above, it can be shown that the activity of the catalysts of the instant invention increases as the length of time in which the supported activated catalyst is being treated in the presence of hydrogen at high temperatures, e.g. 800°–1200°F. increases. This, again, is believed to be due to the fact that the instant invention results in completion of a series of reactions leading to a chemical bonding between the surface of the support and the transition metal and metal constituent of the organometallic compound such that these metals are not free to migrate on the surface of the catalyst and grow large crystallites. The formation of large crystallites in conventional supported catalyst is generally accepted as an important mode of catalyst deactivation. Thus, the catalysts of the instant invention are highly active at extremely mild hydrogenation conditions as well as exhibiting unusual stability at high severity conditions.

The fixation in the presence of hydrogen under the above-described temperature conditions can also be influenced by the hydrogen pressure at which such a treatment is conducted. Generally, atmospheric or near atmospheric pressure, from about 0.5 to about 1.5 atmospheres is employed. However, the hydrogen partial pressure may be increased in the reaction zone up to 100 atmospheres or greater. The hydrogen partial pressure will generally decrease the time-temperature requirements for forming the chemical bonding between the supports at a transition metal and metallic portion of the organometallic compounds.

The so-treated catalysts are then ready for contact with hydrogen or hydrogen-containing gases, a suitable reaction system for producing hydrogenation (or dehydrogenation) reactions. Olefins, whether singular or multiple linkage compounds, aliphatic or cyclic, and containing 2 to about 50 carbon atoms have been readily hydrogenated to paraffins, and aromatic compounds containing from 6 to about 50 carbon atoms, and more preferably from about 6 to about 30 carbon atoms have been saturated to produce the corresponding cycloalkane. Acetylenic compounds, whether singular or multiple linkage, aliphatic or cyclic in containing from about 2 to about 10 carbon atoms can also be hydrogenated by the catalyst of the instant invention. In fact, catalyst formed by the impregnation of the supports with aqueous salts of cobalt, and iron have proven highly satisfactory despite the normally low activity attributed to cobalt and the even lower activity attributed to iron for producing hydrogenation reactions.

The catalysts can be utilized as slurries or as fixed beds, movable beds and fluidized beds, in liquid phase or vapor phase, in batch, continuous or staged operations. Hydrogenation reactions can be carried out at remarkably low temperatures and pressures as contrasted with the more conventional catalysts, whether the reaction is conducted in liquid phase or vapor phase. Hydrogenation reactions are generally conducted at temperatures ranging from about 0°F. to about 1000°F., and preferably at temperatures ranging from about 100°F. to about 500°F. The reaction can be conducted at lower than atmospheric pressures or greater than atmospheric pressures but generally pressures ranging from as low as about 1 atmosphere to about 500 atmospheres can be employed. Preferably, however, pressures ranging from about 1 atmosphere to about 50 atmospheres are employed in conducting the reactions.

These catalysts are suitable for carrying out hydrogenation reactions in systems designed to handle high heats of reaction and severe contacting problems, without substantial deterioration and separation of catalyst from the support. This is due in large part to the high stability and activity of these catalysts, by virtue of which hydrogenation reactions can be conducted at very low hydrogen partial pressures ranging as low as from about 1 to about 200 atmospheres.

When it is desired to carry hydrogenation reactions essentially to completion, an excess of hydrogen over the stoichiometric requirement is used. This excess may vary from a few percent to several hundred or even several thousand percent. In the latter cases, the excess hydrogen is separated and recycled to the system. When it is desired to carry out partial hydrogenations, the reaction can be controlled on the basis of hydrogen concentration, e.g., mol ratio of $H_2$ to feed, or reaction kinetics, e.g., using an excess of hydrogen and controlling reaction by time, temperature, $H_2$ partial pressure and the like.

The activity of the catalyst is virtually unimpaired even after long periods of use. However, there is some interference by some types of sulfur compounds and the normal high activity of the catalyst can be impeded very gradually. Thus, although these catalysts normally have good resistance to sulfur-types and concentrations normally present in petroleum oil stocks, there is evidence that certain sulfur compounds, e.g. mercaptans; tend to be adsorbed on the catalyst and may thereby cause some loss of activity. In addition, impurities such as water, other oxygen-containing compounds and nitrogen-containing compounds may also exert a deactivating effect on the catalysts. Even this effect, however, can be curtailed or eliminated by operating the catalysts at temperatures and pressures at which adsorption of the impurities is not favored. The conditions necessary to achieve this effect will vary with different feedstocks and different impurities.

It has been unexpectedly discovered that the catalyst deactivation is reversible such that the deactivated catalyst can be restored to substantially its original activity, by treatment at elevated temperatures, preferably in the presence of a stripping gas. Examples of suitable stripping gases include hydrogen, nitrogen, methane and the like. Hydrogen is preferred, and is desirably used at temperatures ranging between about 400° and 1000°F. However, broad temperature ranges which are operable in the subject process vary from about 200° to 1200°F. The stripping gases should be substantially free of the impurities that are to be removed from the catalyst, and hence are preliminarily purified such as by drying, caustic scrubbing and drying, contacting with suitable adsorbents and the like. The amount of stripping gas that may be used in the process varies, dependent in part on the degree of deactivation of the catalyst, the level of catalytic activity desired to be obtained and the nature of the stripping gas. In general space velocities ranging between about 100 and 25,000 volumes of gas per volume of catalyst per hour (V/V/Hr), preferably 500 to about 1000 V/V/Hr may be used. The stripping gas may be used on a once-through basis or may be recycled for further use. The reactivation process is desirably conducted in the absence of solvent. In addition, the reactivation process may be aided by conducting same in vacuo. The reactivation is carried out for a time sufficient to achieve the desired level of reactivation and generally for a time ranging between about 1 and 24 hours or more. The catalysts are amenable to substantially complete regeneration by (1) oxidizing with air to remove carbonaceous residues, and (2) reactivation with aluminum alkyl compound.

These and other features of the invention will be understood by reference to the following illustrative examples.

EXAMPLE 1

These examples (1A through 1F, Table I) illustrate the critical properties of the catalyst supports required for this invention. The measurements were made by subjecting the pure, thoroughly dried and deoxygenated supports (no transition metals present) to reaction with aluminum triethyl (in excess). Total gas liberated was metered, collected and analyzed. The total ethane produced is a direct measure of the hydroxyl group content of the support (J. Catalysis 7, 362 (1967)).

The supports, after treatment with excess aluminum triethyl, were heated in nitrogen or hydrogen at 400°F., then cooled and hydrolyzed with excess water. Gases were metered, collected and analyzed. These gases are a quantitative measure of the functional groups associated with the aluminum triethyl fragment (theoretically -$AlEt_2$) now strongly bound to the support. The tendency to form such groups as hydride particularly is a measure of the efficiency with which the supports function to give the catalysts of this invention.

TABLE I

CHARACTERIZATION OF CATALYST SUPPORTS

| Example | Catalyst Support | Hydroxyl Groups, Millimols | | Fixation Conditions | | Hydride Groups after Fixation Millimols/gm. |
|---|---|---|---|---|---|---|
| | | Per Gram | Per Sq. Meter | Atmosphere | Temp.,°F. | |
| A | Alumina F-1 | 1.68 | 0.0060 | Nitrogen | 400 | 0.12 |
| B | Alumina (Alcoholate) | 1.30 | 0.0064 | Nitrogen | 400 | 0.15 |
| C | Alumina (Alcoholate) | 1.28 | 0.0063 | Hydrogen | 400 | 0.14 |
| D | Silica (Gr. 0–8) | 0.06 | 0.00010 | Nitrogen | 400 | 0.004 |
| E | Titania Gel | 0.24 | 0.0022 | Nitrogen | 400 | 0.19 |
| F | Activated Carbon (Columbia-L) | 0.11 | 0.00008 | Nitrogen | 400 | 0.12 |

It is seen from the results given in Table I that both types of activated alumina and titania gel are the best supports. Silica is not a useful support because of its very low hydroxyl content and virtually no tendency to form hydrides. Activated carbon is not a very good support because of its very low hydroxyl content although hydride groups are formed very readily at these hydroxyl sites. However, it will be shown that the performance of activated carbon as a support for the catalysts of this invention can be enhanced by surface oxidation of the carbon.

EXAMPLE 2

One hundred grams of aqueous solution was prepared by dissolving 34 grams $FeCl_3.6H_2O$ in 66 grams of water. One hundred grams F-1 alumina (8–14 mesh) was added to the solution and allowed to stand with occasional mixing for about 30 minutes. A small quantity of liquid was poured off and the catalyst freed of excess liquid by placing on absorbent paper towels. The catalyst was dried for 3 hours in a vacuum oven at 500°F. The recovered catalyst weighed 107.4 grams, and analyzed 5.3 percent iron (calculated as Fe).

A heated quartz reaction tube was charged with 25.7 grams of the above catalyst and a preheat area above the catalyst bed was filled with stainless steel distillation packing. The catalyst was preconditioned in a stream of dry nitrogen at a temperature of 500°–550°F.

for one hour and was then cooled in nitrogen to room temperature. The reactor was flooded from the bottom with a 20% solution of aluminum triethyl. Considerable gas was evolved and the maximum temperature reached 200°F. After 1.33 hours, the solution was withdrawn. A rapid flow of nitrogen was introduced and the temperature was increased to 350°F. Fixation was continued for about 30 minutes.

The temperature in the catalyst bed was adjusted to 250°F. and a 20 percent solution of benzene in cyclohexane was fed at a rate of about 11 cc/hour and hydrogen gas at 60 cc/minute. The pressure in the reaction zone was essentially one atmosphere. Samples analyzed after one hour and two hours on conditions showed no detectable benzene by vapor chromatography, all the benzene having been hydrogenated to cyclohexane.

EXAMPLE 3

A catalyst prepared and activated in a manner essentially identical to that described in Example 2 was used to hydrogenate a feed consisting of 25 percent 1-hexyne in n-heptane at atmospheric pressure in the vapor phase. The catalyst temperature was maintained at 230°–240°F., the liquid fed at 11 cc/hour, and hydrogen gas at 60 cc/minute. The 1-hexyne was hydrogenated completely to n-hexane as shown by vapor chromatography and confirmed by infrared spectroscopy.

EXAMPLE 4

One hundred fifty grams of F-1 activated alumina (8–14 mesh) was treated with 140 grams of an aqueous solution of 36% $CoCl_2 \cdot 6H_2O$. After drying in vacuum for about 5 hours at 400°–450°F., 162.3 grams of intense blue catalyst was obtained. The catalyst contained 5.3% cobalt, calculated as metal.

Twenty-five grams of the above catalyst was charged to a quartz tube and preconditioned at 700°–785°F. in dry nitrogen for approximately 1 hour. After cooling to room temperature in a stream of dry nitrogen, the tube was flooded with a 20% solution of aluminum triethyl in n-heptane. The maximum temperature in the catalyst bed reached 160°F. After about 1 hour, the liquid was withdrawn and the catalyst was fixed in a flow of dry nitrogen at 375°–400°F. for 1 hour. A 20% solution of benzene in cyclohexane was fed at a rate of 11 cc/hour along with 60 cc/minute of hydrogen. At a temperature of 216°–250°F. in the catalyst bed, the benzene was completely hydrogenated to cyclohexane.

EXAMPLE 5

Reagent grade magnesium oxide (50 grams) was mixed with 83 grams of a 40% aqueous solution of $CoCl_2 \cdot 6H_2O$ to give a thick paste. The paste was spread on a glass plate and dried in a vacuum oven at 250°–260°F. for 3 days. The hard particles were crushed in a mortar and 10–20 mesh particles were screened out. These 10–20 mesh particles were dried for 3 hours at 425°–450°F. in the vacuum oven and were light blue in color and contained about 14 percent cobalt calculated as metal.

The quartz reaction tube was charged with 17.3 grams of the above catalyst which was then preconditioned in a stream of dry nitrogen at 660°F. for about 30 minutes. After cooling to room temperature, the tube was flooded with 20% aluminum triethyl in n-heptane. There was very little heat evolved and the liquid was withdrawn after 30 minutes. The catalyst was fixed in dry nitrogen at 350°–365°F.

A 20% solution of benzene in cyclohexane was fed at a rate of 11 cc/hour and hydrogen at a rate of 60 cc/minute. At a catalyst temperature of 240°F., hydrogenation of the benzene was better than 99% complete.

EXAMPLE 6

One hundred grams of F-1 alumina was treated with 80 grams of cobalt octoate solution (6% cobalt dissolved in hydrocarbon vehicle) and the solid dried in the vacuum oven. A second impregnation was carried out in a similar manner and the vacuum dried solid amounted to 113.4 grams.

Twenty-five grams of the above catalyst was charged to the quartz reaction tube, preconditioned in $N_2$ at 500°F. for 2 hours, then activated with 20% aluminum triethyl as previously described and fixed in nitrogen at 400°F. Only very slight hydrogenation of benzene was noted at atmospheric pressure and 240°F. Compared to Example 4, this illustrates the advantage in catalyst activity by carrying out the original impregnation in an aqueous medium with water soluble salts of the transition metal.

EXAMPLE 7

The catalyst described in Example 4 was used to hydrogenate o-xylene (24% in n-heptane) at atmospheric pressure and 260°–270°F. Hydrogenation was complete and two isomers of dimethyl cyclohexane were observed by vapor chromatography.

EXAMPLE 8

Catalysts were prepared and evaluated by the general procedure described in Example 4 with the results shown in Table II; Examples 8A through 8E. All the cobalt catalysts contained about 5% cobalt.

TABLE II

| Example | Catalyst Base | Cobalt Salt Used | Activation Max. Temp. $N_2$ Precond. | AlEt$_3$ Treat | Benzene Hydrogenation at 1 Atm.,250°F. |
|---|---|---|---|---|---|
| 8A | F-1 Alumina | None | 790 | 153 | Not Active |
| 8B | F-1 Alumina | $CoSO_4 \cdot 7H_2O$ | 520 | 140 | 100% |
| 8C | Activated Carbon (Columbia Carbon) | $CoCl_2 \cdot 6H_2O$ | 520 | 121 | 77% |
| 8D | Silica Alumina Cracking Catalyst | $CoCl_2 \cdot 6H_2O$ | 500 | 130 | 77% |
| 8E | F-1 Alumina | Co Acetate $\cdot 4H_2O$ | 500 | 150 | 100% |

EXAMPLE 9

A catalyst consisting of cobalt on F-1 alumina was prepared from aqueous cobaltous acetate according to the procedure of Example 4 and contained 5.3% cobalt (calculated as metal) after drying in the vacuum oven.

The quartz tube reactor was charged with 26.1 grams of the above catalyst which was preconditioned at 600°F. in nitrogen for 1-½ hours, then activated with aluminum triethyl and fixed in hydrogen at 400°F.

A 20% solution of n-butyraldehyde in a n-heptane was hydrogenated at atmospheric pressure with the following results (expressed on solvent-free basis).

| Period | Catalyst Temp., °F. | n-C$_4$ Ald. | Product Analysis, % n-C$_4$ Alc. | Hvy. Prod. |
|---|---|---|---|---|
| 1 | 298 | 0.5 | 91.9 | 7.6 |
| 2 | 300 | 0.5 | 93.2 | 6.3 |
| 3 | 325 | 1.9 | 89.3 | 8.8 |

EXAMPLE 10

A catalyst was prepared by impregnating 100 grams of F-1 alumina with a solution prepared by dissolving 36 grams nickel acetate.4H$_2$O in 156 grams water. After drying in vacuum, the catalyst was impregnated a second time with the residual solution. After drying at 350°–400°F. in vacuum, 116.3 grams catalyst was recovered which analyzed 3.4% nickel (calculated as metal).

The quartz reaction tube was charged with 25.1 grams of the nickel catalyst which was preconditioned in nitrogen at 600°F. (1 hour), then activated with 20% aluminum triethyl (max. temperature 125°F.) and fixed at 400°F. with dry nitrogen.

A 20% solution of C$_4$ aldehydes was hydrogenated at atmospheric pressure, 300°–400°F., 60 cc/minute hydrogen rate. Typical results obtained during an 80-hour run were:

| Aldehyde | n-C$_4$ | n-C$_4$ | iso-C$_4$ |
|---|---|---|---|
| Catalyst Age, Hrs. | 5 | 76 | 46 |
| Aldehyde Feed, W/Hr./W | 0.14 | 0.14 | 0.35 |
| Temperature, °F. Max. | 308 | 309 | 400 |
| Conversion, % | 99.8 | 99.7 | 99.1 |
| Selectivity, % | | | |
| To Alcohol | 95.4 | 97.6 | 96.5 |
| To Heavier Products | 4.6 | 2.4 | 3.5 |

EXAMPLE 11

Fifty grams of activated nickel catalyst prepared as described in Example 10 was charged to a one-liter stirred autoclave along with 240 ml. n-octane and 60 cc. 2-ethyl-hexaldehyde. Five consecutive hydrogenation runs were made using the same charge of catalyst and the same volume of feed. Hydrogenation conditions and results of these five runs are shown below:

| Example | % Aldehyde | Hydrogenation Conditions Temp., °F. | Press. Psig | Hrs.* | % Selectivity to 2-Et. Hexanol |
|---|---|---|---|---|---|
| 11A | 20 | 275 | 500 | 3.5 | 88 |
| 11B | 20 | 294 | 500 | 3.0 | 92 |
| 11C | 20 | 340 | 500 | 1.2 | 97 |
| 11D | 20 | 330 | 200 | 3.0 | 96 |
| 11E | 50 | 330 | 500 | 4.5 | 94 |

*Time until H$_2$ no longer absorbed.

EXAMPLE 12

A commercial cobalt molybdena on alumina catalyst containing about 3.5% CoO and 12% MoO$_3$ and in the form of 1/16 inch extruded rods was charged (36.7 grams) to the quartz reaction tube and was preconditioned in a flow of dry nitrogen at 600°F. for one hour. The catalyst had been calcined at 1200°F. for 12 hours before charging to the tube. After cooling in dry nitrogen, the catalyst bed was flooded with 20% aluminum triethyl. Maximum temperature reached was 160°F. After 40 minutes, the solution was withdrawn and the catalyst fixed at 500°F. in a stream of dry hydrogen for 15 minutes. After cooling, the catalyst was charged with 290 ml. n-octane and 60 ml. benzene to a one-liter stirred autoclave. At a temperature of 225°–230°F. and a pressure of 200 psig, the benzene was completely hydrogenated in 1 hour.

About 80 ml. of the above product was left in the reactor and a fresh charge of 160 ml. octane and 60 ml. benzene was added. This charge was hydrogenated at 165°–170°F. and a pressure of 200 psig and hydrogenation was complete in about 1.5 hours. Selectivity to cyclohexane was essentially 100%.

For comparison purposes, a hydrogen reduced platinum (0.5% Pt) on alumina catalyst used for commercial scale hydrogenation of benzene was tested under conditions identical to the second hydrogenation run described above. Complete hydrogenation of benzene required 2.0 hours.

EXAMPLE 13

A nickel molybdena-alumina commercial hydrotreating catalyst 10–20 mesh particle size and containing 3–4% NiO, 14–16% MoO$_3$ was activated with aluminum triethyl essentially as described in Example 12.

Fifty-three grams of the activated catalyst was charged to the stirred autoclave along with 240 ml. n-octane and 60 ml. benzene. Hydrogenation was carried out at 165°–170°F. and 200 psig and the conversion of the benzene to cyclohexane was complete in 1 hour.

EXAMPLE 14

A catalyst (57 grams), prepared from cobaltous acetate on F-1 alumina and activated according to the procedure of Example 4, was charged to the stirred autoclave along with 240 ml. paraffinic diluent and 60 ml. trans,trans,cis-1,5,9-cyclododecatriene. The hydrogenation conditions were 165–170°F. and 200 psig. Hydrogenation to cyclododecane was 96% complete in 1 hour and complete in 1.33 hours.

EXAMPLE 15

To illustrate the significant effect of type of support used, the following results were obtained using cobalt catalysts (4–5% Co), prepared from cobalt acetate or cobalt chloride (Example 15C). All catalysts were preconditioned in dry nitrogen at 600°F., then activated with aluminum triethyl (20%) as described in previous examples. Finally, the catalysts were fixed in nitrogen at 400°F. Hydrogenations were carried out with 50 ml. portions of catalyst, 240 ml. of paraffinic diluent, and 60 ml. of benzene and the time noted for complete hydrogenation of the benzene at 165°–170°F. and 200 psig.

| Example | Support | Time to Complete Hydrogenation, Hrs |
|---|---|---|
| 15A | F-1 Alumina (Alcoa) | 2.03 |
| 15B | F-10 Alumina (Alcoa) | 1.25 |
| 15C | H-151 Alumina (Alcoa) | 3.22 |
| 15D | 471A Alumina | 5.0 |
| 15E | Alcoholate Alumina | 1.25 |
| 15F | "Celite" (Johns-Manville) | 10.0 |
| 15G | Activated Carbon (Pittsburgh Coke) | 4.75 |

The F-10 alumina and the alcoholate alumina were the purest alumina bases used and these gave the highest catalytic activity. Aluminas containing 2–6% silica (H-151 and 471A) gave less active catalysts. The "Celite" is largely silica and is not a useful catalyst support. The low order of activity is probably due to formation of some cobalt metal rather than to the catalyst complexes of this invention.

EXAMPLE 16

Catalysts containing 5–6% Fe on F-1 alumina were prepared from ferric chloride.6H$_2$O, ferrous chloride.4H$_2$O and ferric nitrate.9H$_2$O and dried in the vacuum oven. The catalysts were preconditioned at 800°F. in dry nitrogen and then contacted with aluminum triethyl at room temperature (maximum temperature during activation was about 200°F.). The catalysts were treated in nitrogen at 400°F. for fixation. Samples were taken after the 800°F. N$_2$ preconditioning and after the final 400°F. N$_2$ fixation for examination by Mossbauer spectrometry to determine the valence state of the iron, and for correlation with catalytic activity. The results obtained were as follows:

| Example | Salt Used In Preparation | Mossbauer Results, % Preconditioned Catalyst Fe$^{+3}$ | Fe$^{+2}$ | Fixed Catalyst Fe$^{+3}$ | Fe$^{+2}$ | Time, Hrs., for Benzene Hydrogenation 165°F. 200 psi |
|---|---|---|---|---|---|---|
| 16A | FeCl$_3$.6H$_2$O | 100 | 0 | 15 | 85 | 1.3 |
| 16B | FeCl$_2$.4H$_2$O | 100 | 0 | 10 | 90 | 1.4 |
| 16C | Fe(NO$_3$)$_3$.9H$_2$O | 100 | 0 | 60 | 40 | (1) |

1. Catalyst not active at 165°F., 200 psig, but benzene hydrogenation was complete in 1.8 hours at 300°F., 400 psig. The catalysts prepared from chloride had high activity and high concentrations of Fe$^{+2}$ in the final activated (fixed) state while the catalyst prepared from nitrate had a much lower order of activity and a much lower concentration of Fe$^{+2}$. No metallic iron was detectable.

EXAMPLE 17

Zinc oxide (442 grams) was mixed with a solution of 93.5 grams nickel acetate.4H$_2$O in 450 ml. warm water to give a thick paste. The mixture was dried in the vacuum oven giving chunks of greenish-white solid. The solid was broken in a mortar and screened to 10–20 mesh size.

The 10–20 mesh catalyst was charged to a heated quartz tube, preconditioned at 600°F. for one hour in a nitrogen atmosphere, then activated with aluminum triethyl and then fixed in nitrogen at 400°F.

The above catalyst (55 grams) was mixed with 250 ml. iso-octane and 50 ml. benzene in a one-liter autoclave and the hydrogenation of the benzene was complete in 5.2 hours at 165°F. and 200 psig.

EXAMPLE 18

These examples show that magnetic susceptibility measurements on typical catalysts of this invention confirm that the group VIII nonnoble metals are present in the +2 valence state. All catalysts were prepared on F-1 alumina base and, containing 4–6% equivalent metal, were activated in the liquid phase with triethyl aluminum (20% solution), then fixed in a nitrogen atmosphere at 400°F. The iron catalysts derived from FeCl$_3$ and Fe(NO$_3$)$_3$ were the same catalysts in which the Mossbauer measurements described in Example 16 were made.

| Salt Used to Impregnate Base | Magnetic Moment, $\mu$ after Activation and Fixation | Literature Values Fe$^{+2}$ | Fe$^{+3}$ |
|---|---|---|---|
| FeSO$_4$ | 5.18 | 5.1 | 5.9 |
| FeCl$_3$ | 5.35 | | |
| Fe(NO$_3$)$_3$ | 5.29 | | |
| | | Ni$^{+2}$ | |
| NiSO$_4$ | 2.92 | 3.1 | |
| | | Co$^{+2}$ | |
| CoSO$_4$ | 4.79 | 5.2 | |

Literature values are for these elements in octahedral configuration. For the iron catalysts, the values are in good agreement for predominantly an Fe$^{+2}$ configuration but containing a small amount of Fe$^{+3}$ contaminant (as shown by the Mossbauer data in Example 16). Only in the case of the catalyst derived from Fe(NO$_3$)$_3$ was a minute trace (about 85 ppm) of metallic iron detected.

The nickel and cobalt catalysts (Ni$^{+2}$ and Co$^{+2}$ salts used in preparation) one in fairly good agreement but slightly lower in magnetic moment than the literature values. It is well known that distorted configurations such as would exist on a support surface will lower the magnetic moment.

EXAMPLE 19

A catalyst containing 6.5 weight % iron was prepared by impregnating an alcoholate type alumina with aqueous iron nitrate. In the following table the benzene hydrogenation activity of this catalyst, activated in accordance with this invention (preconditioned at 800°F. in N$_2$ and fixed as indicated), is compared with the activity of the same catalyst activated by severe hydrogen treating.

| Example | 19A | 19B | 19C |
|---|---|---|---|
| Catalyst | 6.5% Fe on PF Alumina | | |
| AlEt$_3$ Treat | None | Standard Treat | |
| Fixation (H$_2$ Atm.) Temp., °F. | 1200 | 400 | 1200 |

-continued

| Example | 19A | 19B | 19C |
|---|---|---|---|
| Time, Hrs. | 16 | 1 | 16 |
| Mossbauer Summary Estimated % of Fe as | | Before AlEt₃ Treat | After Fixation | After Fixation |
| $Fe^{+3}$ | — | 85 | 65 | 50 |
| $Fe^{+2}$ | — | — | 25 | 20 |
| Alpha $Fe_2O_3$ | — | 15 | — | — |
| Alpha Fe | — | — | 10 | 30 |
| Time, Hrs., to Compl. | 1000+ | | 3.2 | 3.3 |
| Abs. Hydro. Act.mol/hr/gm Fe | <0.0001 | | 0.34 | 0.37 |

The catalyst activated by hydrogen alone is essentially inactive for benzene hydrogenation (at 212°F., 600 psig). There are only slight differences in activity between the mildly fixed (400°F.) and severely fixed (1200°F.) catalysts. The Mossbauer results (presence of alpha iron) indicate that this catalyst contained too high an iron concentration for maximum activity and complete stabilization.

EXAMPLE 20

A catalyst similar to that of Example 19 was prepared from iron nitrate on the same alumina base, except that the iron content was 3.2 wt. %. This catalyst was activated according to the procedure used for Example 19B, activity for benzene hydrogenation was 0.04 mol/hr./gm. Fe at 212°F. and 0.38 mol/hr./gm. Fe at 300°F. The same charge of catalyst was placed back in the tube and heated in hydrogen for 16 hours at 1200°F. The hydrogenation activity tests were repeated. At 212°F. the activity was 0.54 mol/hr./gm. Fe and at 300°F. was 2.4 mol/hr./gm. Fe. At this more optimum iron concentration and more optimum Al/Fe ratio, the stabilization of the iron by the aluminum is much more complete and the actiity is enhanced on the order of tenfold or more.

EXAMPLE 21

A series of iron catalysts containing 0.8, 1.6, 3.2 and 6.4 percent Fe were prepared on the alcoholate type alumina base. The base contains 1.2 millimols/gm. —CH group equivalent and the Fe was impregnated on the base as $FeCl_3 \cdot 6H_2O$. The catalysts were activated by preconditioning at 600°F. ($N_2$ atmosphere), treating with 20 percent AlEt₃ in n-heptane, then fixed in hydrogen at 400°F. Activities were determined on an absolute basis (mols. benzene hydrogenated per hour per gram Fe) in a standard hydrogenation test at 212°F. and 600 psi $H_2$ pressure. Results of these tests were:

| Run | Wt. % Fe | Mole Ratio Fe/OH | Hydrogenation Rate, mol/hr./gm. Fe | |
|---|---|---|---|---|
| | | | 212°F. | 300°F. |
| A | 6.4 | 1.01 | 1.94 | — |
| B | 3.2 | 0.49 | 2.60 | — |
| C | 1.6 | 0.24 | 1.11 | — |
| D | 0.8 | 0.12 | 0.17 | 1.18 |

The results are very striking in showing the critical effect of transition metal/hydroxyl group ratio in preparing these catalysts. There is a fairly sharp maximum in catalytic activity occuring at an Fe/OH molar ratio of about 0.5. However, even at the greatly nonoptimum ratio of 0.12, the activity of catalyst is increased more than six-fold by increasing the temperature to 300°F.

EXAMPLE 22

This example is to show the positive identification of Fe-Al linkages in high activity iron catalysts prepared according to this invention. Also, it is designed to show the amount of iron present in the active catalytic state. The method is based on hydrolysis of the activated, fixed catalysts with deuterium oxide, and that (1) hydride groups on Al or Fe will give HD on deuterolysis, and (2) -Al-Fe direct linkages will give $D_2$ on deuterolysis. Thus the $D_2$ make will be a direct measure of -Al-Fe groups.

The two most active catalysts from Example 21 (6.4% Fe and 3.2% Fe preconditioned at 600°F.) were used in these tests. All gases liberated during the treat with 20% AlEt₃, during the hydrogen fixation and during the deuterolysis with excess $D_2O$ were metered, collected and analyzed. The deuterolysis gases were analyzed for HD, $D_2$ and deuterated components of methane and ethane in addition to the usual components. Results of these exhaustive tests for the two iron catalysts were:

| Example | 22A | 22B |
|---|---|---|
| Catalyst, Wt. % Fe | 6.4 | 3.2 |
| Total Deuteralysis Gas, mmol./gm. Cat | 1.52 | 1.78 |
| $D_2$ Made, mmol./gm. Cat. | 0.41 | 0.34 |
| HD Made, mmol./gm. Cat. | 0.34 | 0.39 |
| $D_2$, Mole % on Fe | 36 | 59 |
| Hydrogenation Activity, mol./hr./gm. Fe | 1.94 | 2.60 |

The $D_2$ concentration expressed as mol % on Fe represents the percent of iron as the catalytically active species, that is, having an average of one iron to aluminum direct chemical bonds. The catalyst bonding the greater percent iron in this form is the same as the catalyst of Example 21 Run B.

EXAMPLE 23

To illustrate the criticality of preconditioning the catalyst at elevated temperatures, the catalyst containing 6.4% Fe (as $FeCl_3$) on the PT (alcoholate) alumina base was activated as described in Example 21 except that the temperature of preconditioning was varied from 300°F. to 600°F. to 900°F. in nitrogen atmosphere for 2-hour periods. Activity was measured by the benzene hydrogenation test.

| Example | Preconditioning Temp., °F. | Absolute Hydrogenation Rate, Mol./Hr./Gm. Fe |
|---|---|---|
| 23A | 300 | 0.26 |
| 23B | 600 | 1.94 |
| 23C | 900 | 1.60 |

These results show clearly that an inferior catalyst results at low pretreat temperatures. At the highest temperature, 900°F., some crystallite growth may have occurred since the high stability characteristic of these catalysts is not realized prior to the alkyl treat and fixation in the presence of hydrogen.

EXAMPLE 24

A catalyst containing 6.5% Fe was prepared by impregnating silica gel (Davison Grade 0–8) with $FeCl_3$ aqueous solution. The catalyst was preconditioned at 800°F., treated with 20% $AlBt_3$ solution, then fixed in hydrogen at 400°F. Activity for benzene hydrogenation was not measurable at 212°F. and was on the order of 0.002 mol./hr./gm. Fe at 300°F. This silica-based catalyst is essentially inactive because any hydroxyl groups in the silica base undergo alkylation to give -Si-Et groups rather than the necessary -Si-O-$AlBt_2$ groups.

EXAMPLE 25

This example is designed to show the importance of hydroxyl functionality on a support such as activated carbon. Columbia activated carbon Grade L (surface area 1350 sq.in./gm.) was impregnated with an aqueous solution of ferric chloride to give 6.0 wt. % Fe. Another sample of the carbon was air-oxidized at 500°F. for 16 hours and then impregnated to give 6% Fe. Both catalysts were preconditioned for 2 hrs. at 600°F. in $N_2$ atmosphere, treated with triethyl aluminum (20% solution), then fixed in hydrogen for 1 hour at 400°F. Benzene hydrogenation activities were as follows for these catalysts.

| Benzene Hydrogenation Temperature,°F. | Hydrogenation Activity, mol./hr./gm. Fe | |
|---|---|---|
| | Carbon Base Not Preoxidized | Carbon Base Preoxidized |
| 212 | 0.023 | 0.040 |
| 300 | 0.053 | 0.130 |
| 392 | 0.155 | 0.360 |

Preoxidation of the carbon base more than doubles the activity of the catalysts. However, compared to activated alumina, carbon is a relatively poor base for these catalysts because its hydroxyl functionality is far from optimum, even after oxidation.

EXAMPLE 26

A titania gel base having a surface area of 106 sq. meters/gm. was determined to have a hydroxyl group content of 0.24 millimols/gm. as described in Example 1. This base (100 grams) was impregnated with a solution prepared by dissolving 17 gms. $FeCl_3.6H_2O$ sufficient water to give 65 cc. of solution. Essentially all the solution was absorbed and the iron content of the catalyst was 3.2 wt. % after drying in the vacuum oven.

A 50 cc. portion of the catalyst was activated as follows: (a) preconditioned at 600°F. for 2 hours in a flow of dry nitrogen; (b) treated with an excess of 20% $AlEt_3$ solution-maximum temperature was 192°F.; and (3) fixation in hydrogen for one hour at 400°F.

The activated catalyst (56.4 gms.) was charged with 250 cc. of benzene to the stirred autoclave and a hydrogenation test carried out at 212°F. and 600 psig $H_2$ pressure. The hydrogenation was complete in 1½ hours and the catalytic activity calculated to be 1.03 mol./hr./gm. Fe.

EXAMPLE 27

The iron catalyst containing 3.2% Fe derived from iron nitrate on the alcoholate alumina base was activated with diethyl zinc and triethyl boron in comparison with triethyl aluminum. The catalyst preconditioning activation and fixation conditions and hydrogenation activities were as shown in the table below:

| Example | 27A | 27B | 27C |
|---|---|---|---|
| Alkyl Used | $AlEt_3$ | $BEt_3$ | $ZnEt_2$ |
| Preconditioning Temp., °F. | 600 | 600 | 600 |
| Alkyl Treat, temp., °F. (Max) | 200 | 550 | 190 |
| Fixation ($H_2$ Atm.) | | | |
| Temp., °F. | 400 | 400 | 1200 |
| Time, Hrs. | 1 | 1 | 16 |
| Hydrogenation Activity, mol./hr./gm. Fe | 0.38 | 0.031 | 0.11 |
| At Temp., °F. | 300 | 392 | 392 |

EXAMPLE 28

The catalyst having a very low nickel concentration (0.6 Wt. % Ni) was prepared by impregnating the alcoholate alumina base with an aqueous solution of nickelous acetate. Hydrogenation activities for activation with hydrogen alone and by the method of this invention are compared in the table.

| Example | 28A | 28B | 28C |
|---|---|---|---|
| Catalyst | 0.6% Ni on PF Alumina | | |
| $AlEt_3$ Treat | None | Standard | |
| Fixation ($H_2$ Atm.) | | | |
| Temp., °F. | 1200 | 400 | 1200 |
| Time, Hrs. | 16 | 1 | 16 |
| Time, Hrs. to Completion | 45 | 5.3 | 3.2 |
| Abs. Hydro. Act., mol/hr/gm Ni | 0.31 | 2.2 | 3.7 |

EXAMPLE 29

The noble metals of Group VIII are also converted to highly active and stable catalyst by the technique of this invention. However, the noble metals, because of cost and activity considerations, are generally used in very low concentrations, e.g., 0.1–1.0%, on the support. With the usual supports, this results in very high alkyl metal-to-noble metal molar ratios (e.g., 20/1 to 100/1). Under such conditions and at mild fixation severity, the noble metal may be overwhelmed or buried by the alkyl metal resulting in low catalyst activity. But it has been found that at very severe fixation conditions this effect is overcome and highly active and extremely stable catalysts result.

A 0.6% platinum on alcoholate alumina was prepared by impregnation with aqueous chloroplatinic acid. The activity of this catalyst at several severities of hydrogen activation was as follows:

| Example | 29A | 29B | 29C |
|---|---|---|---|
| Catalyst | 0.6% Pt on Alcoholate Alumina | | |
| $H_2$ Reduction Cond. | | | |
| Temp., °F. | 800 | 1200 | 1200 |
| Time, Hrs. | 2.5 | 2.5 | 18.5 |
| Time, Hrs. to Compl. | 0.90 | 1.33 | 1.75 |
| ABS Hydro. Act.* | 22.8 | 18.0 | 12.2 |

*Mol./hr./gm. Pt.

The decreasing activity with increasing severity of hydrogen reduction is attributed to growth of larger crystallites of platinum metal. It was, however, not possible to detect this by X-ray at this low platinum concentration.

Here it is noted that the activity of the catalyst is increasing with increasing hydrogen fixation severity and that the low activity characteristic of mild fixation 3. Fixation in hydrogen compared to fixation in nitrogen at high severity.
4. The activation method of this invention is inhibiting formation of large crystallites of transition metals (free metals).

| Example | 31A | 31B | 31C | 31D | 31E | 31F |
|---|---|---|---|---|---|---|
| Cat. Activation AlEt₃ Treat | None | | | Standard Treat[a] | | |
| Fixation Atmosphere | | | Hydrogen | | | Nitrogen |
| Temp., °F. | 1200 | 1200 | 400 | 900 | 1200 | 800 |
| Time, Hrs. | 16 | 44 | 1 | 16 | 16 | 16 |
| Hrs. to Completion | 69 | 91 | 3.3 | 1.83 | 1.60 | 6.6 |
| Abs. Hydro. Act.[b] | 0.012 | 0.0096 | 0.27 | 0.42 | 0.53 | 0.12 |
| Rel. Mo Metal[c] | 0.69 | 1.00 | 0.000 | — | 0.036 | 0.012 |

[a]Catalyst heated at 800°F. in N₂ flow for 2 hours, cooled, treated with an excess of 20% AlEt₃ at room temperature.
[b]Mols benzene hydrogenated per hour per gram of metal.
[c]By x-ray diffraction, relative values based on most severely reduced catalyst = 1.00.

| Example | 29D | 29E | 29F | 29G |
|---|---|---|---|---|
| Catalyst | 0.6% Pt on Alcoholate Alumina | | | |
| AlEt₃ Treat | Standard | | | |
| Fixation (H₂ Atm.) | | | | |
| Temp., °F. | 400 | 800 | 1200 | 1200 |
| Time, Hrs. | 1 | 2.5 | 16 | 32 |
| Time, Hrs. to Compl. | 53 | 15.8 | 1.6 | 0.67 |
| ABS Hydro. Act. mol/hr./gm. Pt | 0.37 | 1.40 | 11.8 | 17.2 |

(Example 29D) is completely overcome. The extreme stability of the catalyst of Example 29G is typical of noble metal catalysts activated by the methods of this invention. An equivalent time-temperature exposure in hydrogen activation (or reactions with hydrogen) would give a predicted activity in the range of 5–7 mol/hr./gm. Pt.

EXAMPLE 30

A molybdenum catalyst containing 13 wt. % MoO₃ was prepared by impregnating 200 grams of the alcoholate alumina base with a solution of 38 grams ammonium molybdate (82% MoO₃) dissolved in 120 cc. water. All liquid was absorbed and the catalyst was dried in the vacuum oven.

A 50 cc. portion of this catalyst was charged to the quartz tube and heated in a flow of dry nitrogen at 800°F. for 2 hours. After cooling to room temperature, the catalyst was treated with 20% triethyl aluminum giving a transient maximum temperature of 195°F. After one hour, the liquid was withdrawn and the catalyst was fixed in hydrogen at 400°F. for 1½ hours.

Thirty-nine grams of the activated catalyst and 250 cc. of benzene were charged to a stirred autoclave and a hydrogenation was carried out at 212°F. and 600 psig H₂ pressure. The reaction was complete in 3 hours and the calculated rate of hydrogenation was 0.28 mol benzene hydrogenated per hour per gram of molybdenum.

EXAMPLE 31

In the data tabulated below, the 13% MoO₃ on alcoholate alumina catalyst is used to show the effects of
1. Hydrogen activation vs. the activation method of this invention.
2. Increasing severity of fixation in a hydrogen atmosphere.

Examples 31C, D and E show the effects of increasing severity of fixation in the presence of hydrogen.

Examples 31C, D, and E, in comparison with Examples 31A and B, show the activation method of this invention in comparison with hydrogen activation. The x-ray diffraction data for these runs show how the technique of this invention stabilizes the active catalytic species in a very stable, highly dispersed form.

Examples 31D and F show the effects of fixation in nitrogen compared to fixation in hydrogen and that the presence of hydrogen during fixation results in a significant increase in the hydrogenation activity of the catalyst.

EXAMPLE 32

A catalyst containing about 10 wt. % tungsten was prepared by impregnating 200 gms. of alcoholate type alumina with an aqueous solution prepared by dissolving 31 grams of ammonium meta tungstate in 110 cc. water. All solution was taken up.

A 50 cc. portion of the above catalyst was changed to an electrically heated quartz tube and heated at 850°F. in a flow of dry nitrogen for 3 hours.

After cooling to room temperature, the catalyst bed was flooded from the bottom with a °% solution of triethyl aluminum in n-heptane. The temperature rose transiently to 190°F. and much gas was evolved. After 30 minutes the solution was drained off and the catalyst was then heated in nitrogen at 400°–420°F. for one hour.

Forty grams of the above catalyst and 250 cc. benzene were charged to a stirred autoclave and a hydrogenation was carried out at 212°F. and 600 psig H₂ pressure. Gas was absorbed at a rate of 20 lbs. per minute and the reaction was complete in 4.1 hours. The absolute rate of hydrogenation was calculated to be 0.17 mole of benzene hydrogenated per hour per gram of tungsten.

Another run made with the same catalyst at 260°F. gave a hydrogenation rate of 0.31 mol/hr./gm. of tungsten.

EXAMPLE 33

The results tabulated below were obtained with two tungsten catalysts on alcoholate type alumina having respective tungsten concentrations of 27 percent WO₃ and 9 percent WO₃. These results will show the effects of the concentration of the transition metal, in this case, tungsten.

| Example | 33A | 33B | 33C | 33D | 33E | 33F |
|---|---|---|---|---|---|---|
| $WO_3$ conc., wt. % | 27 | 27 | 27 | 9 | 9 | 9 |
| Activation $AlEt_3$ Treat | None | Standard | | None | Standard | |
| Fixation ($H_2$) | | | | | | |
| Temp., °F. | 1200 | 400 | 1200 | 1200 | 400 | 1200 |
| Time, Hrs. | 16 | 1 | 16 | 16 | 1 | 16 |
| Hrs. to Compl. | 153 | 3.6 | 77 | 1000 | 5.6 | 5.7 |
| Abs. Hydro. Act., Mol/hr./gm. W | 0.0017 | 0.057 | 0.0028 | 0.0001 | 0.18 | 0.18 |
| X-Ray Eval. | Most W metal also $WO_2$ & $W_3O$ W>$WO_2$ or ≅$W_3O$ | No cryst. forms of W metal oxides. | W metal, possibly $WO_2$ & $W_3O$. conc. | No W metal possible small Ex.33D $WO_2$ | No W metal less $WO_2$ than or | No cryst. form of W metal oxides. |

Examples 33A, B and C with the high tungsten concentration show that the $AlEt_3$ activated, hydrogen fixed catalyst (Example 33B) is more than 50 times as active as the catalyst activated by hydrogen (Example 33A). However, this catalyst is unstable at higher severity hydrogen fixation. The Al/W ratio (Al from $AlEt_3$) is insufficient to stabilize this amount of tungsten.

The Al/W ratio is much more favorable at the 9% $WO_3$ concentration and most of the tungsten is stabilized, does not undergo crystallite growth, and activity remains constant as fixation severity is increased (compare Example 33F with Example 33E).

EXAMPLE 34

Results obtained at a still lower tungsten concentration (6% $WO_3$ on the alcoholate alumina base) show a striking enhancement in activity as fixation severity is increased.

This catalyst, when given the standard $AlEt_3$ activation (as in Example 33) and fixed in hydrogen for 1 hour at 400°F., had a benzene hydrogenation activity of 0.10 mol/hr./gm. W. The same catalyst was then placed back in the activation tube and given an additional fixation of 16 hours at 1200°F. in hydrogen. This catalyst then showed an activity of 0.71 mol/hr./gm. W. This high activity is now completely stabilized.

EXAMPLE 35

A catalyst was prepared by impregnating 200 gms. of F-1 alumina with a solution of 3 ml. perrhenic acid (1.3 gms. Re/ml.) made up to 120 ml. with water. All solution was absorbed. Catalyst was dried in the vacuum oven and had a rhenium content of 2.0 wt. %.

The quartz activation tube was charged with 55 cc. of the above catalyst and heated in a flow of dry nitrogen at 600°F. for 2 hours. After cooling to room temperature, the catalyst bed was flooded from the bottom with a 20% solution of aluminum triethyl. The maximum temperature reached 210°F. After one hour, the solution was drained off and the catalyst was fixed in hydrogen for one hour at 400°F.

The stirred autoclave was charged with 51.5 gms. of the above catalyst and 250 cc. of a 20% solution of benzene in n-octane.

At a temperature of 260°F. and a hydrogen pressure of 500 psig, the benzene was hydrogenated at a rate of 0.22 mol/hr./gm. Re.

EXAMPLE 36

A catalyst was prepared by impregnating 200 gms. F-1 alumina with a solution prepared by dissolving 40 gms. $C_RO_3$ in sufficient water to give a total volume of 125 ml. All liquid was absorbed. The catalyst was dried in the vacuum oven and the chromium content was 9 wt. %.

The catalyst (60cc.) was activated as follows: (1) heated in air for 16 hours at 1000°F.; (2) heated in dry nitrogen for 1 hour at 1000°F.; (3) cooled to room temperature and treated with an excess of aliminum triethyl (20% solution), maximum temperature reaching 240°F; and (4) finally treating in hydrogen for 2 hours at 400°F.

The activated catalyst (49 gms.) was charged to the stirred autocalve with 250 cc. benzene. Hydrogenation at 300°F. and 600 psig $H_2$ pressure gave a measured reaction rate of 0.062 mol of benzene hydrogenated per hour per gram of chromium.

EXAMPLE 37

A catalyst was prepared by impregnating 200 gms. of alcoholate type alumina with a solution of 38 gms. ammonium vanadate dissolved in a mixture of 80 cc. of water and 60 cc. of monoethanolamine, the latter added to aid in dissolving the ammonium vanadate. After drying in the vacuum oven, the catalyst contained 7.5% vanadium.

The catalyst was activated as follows: (1) heated in air for 7½ hours at 1000°F.; (2) heated in dry nitrogen for 1 hour at 800°F.; (3) cooled to room temperature and treated with an excess of aluminum triethyl (20% solution), maximum temperature reaching 205°F.; and (4) fixation in hydrogen at 400°F. for 1 hour.

The activated catalyst (41 gms.) was charged to the autoclave with 250 cc. of benzene. Hydrogenation at 212°F. and 600 psig $H_2$ pressure gave a hydrogenation rate of 0.08 mol/hr./gm. vanadium and at 300°F. and 600 psig the rate increased to 0.21 mol/hr./gm.

EXAMPLE 38

A catalyst containing 6 wt. % copper was prepared by impregnating 200 gms. F-1 alumina with a solution prepared by dissolving 34 gms. $CuCl_2-2H_2O$ in sufficient water to give 160 cc. solution. All solution was absorbed and the catalyst was dried in the vacuum oven.

The activation tube was charged with 47.2 gms. of the catalyst, the weight being determined after preconditioning the catalyst at 800°F. for 2 hours in dry nitrogen. The catalyst was then activated with an excess of aluminum triethyl and fixed in hydrogen at 400°F. for one hour.

The fixed catalyst was then hydrolyzed with deuterium oxide and gases evolved were collected and analyzed. The gases were principally $C_2H_5D$, $D_2$ and HD, the latter two components amounting to 0.18 and 0.07 millimols per gram of catalyst, respectively. This amount of $D_2$ corresponds to 19 percent of the copper bonded directly to aluminum and an average of 4 mol % hydride (bases on copper) associated with the copper-aluminum complex.

This catalyst had relatively low activity for hydrogenation of benzene, the activity being determined as 0.033 mol/hr./gm. Cu at 392°F. and 600 psig $H_2$ pressure.

EXAMPLE 39

A catalyst containing 6 wt. % manganese was prepared by impregnating 200 gms. of alcoholate alumina with a solution prepared by dissolving 54 gms. manganous acetate (4 $H_2O$) in sufficient water to give 225 cc. of solution. Essentially all liquid was absorved and the catalyst was dried in the vacuum oven.

A 50 cc. portion of the catalyst was placed in the heated quartz tube and preconditioned at 800°F. in a flow of dry nitrogen for 2 hours. The temperature was then reduced to 400°F. and aluminum triethyl (20%) solution was added dropwise over a period of one hour. The temperature maximum was 565°F. Aftr one hour the alkyl solution was cut off and the catalyst was fixed at 400°F. in a stream of dry hydrogen.

Thirty-six grams of the activated catalyst was charged to the stirred autoclave with 250 cc. benzene. At 392°F. and 600 psig $H_2$ pressure, the hydrogenate rate was 0 015 mol/hr./gm. Mn.

EXAMPLE 40

A catalyst containing about 7 wt. % mickel was prepared by three consecutive impregnations of 500 gms. F-1 alumina with solutions containing 50 gms. nickel acetate (.4$H_2O$) in sufficient water to give 250 cc. solution. The catalyst was dried in the vacuum oven between impregnations.

The activation tube was charged with 50 cc. of this catalyst which was preconditioned by heating at 800°F. for 2 hours in a flow of dry nitrogen. After cooling to room temperature, the catalyst was treated with an excess of a 20% solution of diethyl aluminum fluoride in n-heptane. After standing for about 1 hour, the solution was drawn off and the catalyst was fixed in a flow of dry nitrogen at 400°F. for 1 hour. The catalyst was analyzed and contained 6.4% nickel and 2.5% fluorine.

The stirred autoclave was charged with 43.4 gms. of the above activated catalyst and 250 cc. of benzene and a hydrogenation reaction was carried out at 212°F and 600 psig $H_2$ pressure. The hydrogenation rate of the benzene was 0.39 mol/hr./gm. Ni.

EXAMPLE 41

The following example demonstrates the effectiveness of the reactivation process of the subject invention. A catalyst containing about 10 wt. % tungsten, based on total weight of catalyst, on alcoholate alumina was prepared by impregnating the alumia base with an aqueous solution of ammonium meta tungstate and drying in a vacuum oven. The catalyst was activated as follows:

Fifty (50) cc of the catalyst was charged to a quartz tube and heated in a stream of dry nitrogen for two hours and cooled under nitrogen. The tube and catalyst bed were then flooded from the bttom with a 20% solution of triethyl alunimum in n-heptane. A vigorous reaction occurred with considerable gas liberation and the temperature rose from room temperature to about 190°F. After the reaction subsided the solution was withdrawn. The catalyst was subsequently fixed by heating in a flow of dry hydrogen at 400°F. for one hour and then cooled under dry nitrogen.

The catalyst as prepared above was charged to a 1-liter stirred autoclave with 250 cc of benzene and a hydrogenation reaction conducted at 212°F. and 500–600 pounds of hydrogen pressure. The hydrogenation of the benzene followed zero order kinetics. After the reaction was substantially complete, the liquid product was withdrawn from the autoclave and a fresh charge of 250 cc of benzene introduced therein. Additional cyclic batch hydrogenation runs were carried out in the same manner. Catalyst deactivation was determined by the change in rate constant with cycles of operation at 212°F. Typical results are shown below:

| HYDROGENATION CYCLE | ZERO ORDER RATE CONSTANT %/HR. |
|---|---|
| NUMBER | |
| 1 | 23.7 |
| 3 | 13.0 |
| 4 | 8.8 |

After the fourth cycle, the catalyst was placed back in the quartz tube and treated at 600°F. for one hour in a flow of dry hydrogen. The regenerated catalyst was charged to the autoclave with a fresh 250 cc charge of benzene. A hydrogenation rate constant of 22.7 was determined at 212°F. and 500–600 psi hydrogen pressure, indicating that the catalyst had been regenerated to very near its initial activity.

What is claimed is:
1. A process for the hydrogenation of a feed containing benzene comprising the steps of:
forming a catalyst by
impregnating a support containing at least about 0.1 millimoles of hydroxyl groups per gram of support, said support comprising alumina with an aqueous solution of a transition metal salt comprising nickel acetate;
heat-treating the impregnated support at a temperature of at least about 500°F.;
activating the heat-treated impregnated support by contacting same with an organometallic compound having the formula: $QR_n$, wherein Q is selected from Group I, II or III metals of the Periodic Chart of the Elements, R is selected from the group consisting of hydride and alkyl, aryl, alkaryl, aralkyl and cycloalkyl radicals containing from 1 to about 20 carbon atoms and wherein N ranges from 1 to 3 and satisfies the valence of Q;
treating the activated supported metal complex in the presence of hydrogen at a temperature of at least about 300°F,;
and thereafter contacting said catalyst with said feed in the presence of a hydrogen-containing gas, thereby producing a hydrogenation reaction.
2. The process of claim 1 wherein the hydrogenation reaction is conducted at a temperature in the range of from about 0° to about 1000°F. and at a pressure rang- ing between about 1 and 50 atmospheres.

3. The process of claim 1 wherein said catalyst is at least partially deactivated as a result of contacting same with said feed in the hydrogenation reaction, and where said deactivated catalyst is at least partially reactivated by treatment of same at eleated temperature in the presence of a stripping gas.

4. The process of claim 3 wherein said stripping gas is selected from the group consisting of hydrogen, nitrogen and methane.

5. The process of claim 4 wherein said stripping gas is hydrogen.

6. The process of claim 3 wherein said elevated temperatures range between about 200° to 1200°F.

7. The process of claim 3 wherein the space velocity of the stripping gas ranges from about 100 to about 25,000 volumes of gas per volume of catalyst per hour.

8. The process of claim 1 wherein said catalyst is at least partially deactivated as a result of contacting same with said feed in the hydrogenation reaction, and where said deactivated catalyst is at least partially regenerated by (1) oxidizing same with air and (2) reactivating by contacting said oxidized catalyst with a trialkyl alunimum compound wherein the alkyl group contains from 1 to about 6 carbon atoms.

9. The process of claim 1 wherein Q has an atomic number of from 3 to 50, and wherein $QR_n$ is a trialkyl aluminum compound.

10. The process of claim 1 wherein the activated supported metal complex is treated in the presence of hydrogen at a temperature above about 800°F.

11. The process of claim 1 wherein the amount of transition metal impregnated on the support is in the range of from about 0.1 to about 30% bases on total weight of deposited equivalent metal and support.

12. The process of claim 1 wherein said alumina support has a surface area greater than about 100 square meters per gram of support and a hydroxyl content of at least one millimole per gram of support.

13. The process of claim 12 wherein said impregnated support is heat-treated at a temperature of about 800°F.

14. The process of claim 12 wherein said heat-treated impregnated support is activated by contacting same with an organometallic compound comprising aluminum triethyl and wherein the activated supported metal complex is treated in the presence of hydrogen at a temperature of at least about 400°F.

15. The process of claim 14 wherein the aluminum triethyl is present in a paraffinic diluent in a concentration of about 20 wt. % aluminum triethyl in the diluent.

16. The process of claim 1 wherein said impregnated support is heat-treated at a temperature ranging between about 600° and 1500°F. in order to remove liquid and adsorbed oxygen therefrom.

* * * * *